US009283327B2

(12) United States Patent
Hourmand et al.

(10) Patent No.: US 9,283,327 B2
(45) Date of Patent: Mar. 15, 2016

(54) AUTO-INJECTOR

(75) Inventors: Yannick Hourmand, Halsingfield (GB); Timothy Donald Barrow-Williams, Herts (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 238 days.

(21) Appl. No.: 13/993,531

(22) PCT Filed: Dec. 21, 2011

(86) PCT No.: PCT/EP2011/073503
§ 371 (c)(1),
(2), (4) Date: Jun. 12, 2013

(87) PCT Pub. No.: WO2012/085022
PCT Pub. Date: Jun. 28, 2012

(65) Prior Publication Data
US 2013/0267909 A1 Oct. 10, 2013

Related U.S. Application Data

(60) Provisional application No. 61/432,254, filed on Jan. 13, 2011.

(30) Foreign Application Priority Data

Dec. 21, 2010 (EP) ..................................... 10196068

(51) Int. Cl.
*A61M 5/32* (2006.01)
*A61M 5/20* (2006.01)

(52) U.S. Cl.
CPC ........... *A61M 5/3245* (2013.01); *A61M 5/2033* (2013.01); *A61M 5/326* (2013.01); *A61M 2005/206* (2013.01); *A61M 2005/208* (2013.01)

(58) Field of Classification Search
CPC ....... A61M 5/20; A61M 5/2033; A61M 5/24; A61M 5/3232; A61M 5/3234; A61M 5/3257–5/3272; A61M 2005/2026; A61M 2005/206; A61M 2005/2013; A61M 2005/208; A61M 2005/3235; A61M 2005/3239

See application file for complete search history.

(56) References Cited

U.S. PATENT DOCUMENTS

2002/0095120 A1   7/2002   Larsen et al.
2005/0273055 A1   12/2005   Harrison et al.

(Continued)

FOREIGN PATENT DOCUMENTS

EP          0666084         8/1995
WO          2005025636      3/2005

(Continued)

OTHER PUBLICATIONS

International Search Report for Int. App. No. PCT/EP2011/073503, completed Mar. 9, 2012.
International Search Report issued in PCT/EP2011/073505 on Jun. 6, 2012.

*Primary Examiner* — Laura Bouchelle
(74) *Attorney, Agent, or Firm* — Fish & Richardson P.C.

(57) ABSTRACT

According to the invention, an auto-injector for administering a dose of a liquid medicament (M) comprises of a substantially cylindrical housing arranged to contain a pre-filled syringe; a syringe retainer slidably arranged with respect to the housing that mounts a pre-filled syringe with an injection needle, a plunger and a stopper for sealing a syringe barrel of the pre-filled syringe; a coupling shroud slidably arranged within the housing and releasably coupled to the plunger; and a single drive means. Upon release, the single drive means is capable of driving the coupling shroud in the proximal direction (P). The proximal translatory movement of the coupling shroud with respect to the housing, translates the syringe retainer in the proximal direction (P) to expose the injection needle of the pre-filled syringe, depresses the plunger connected to the stopper into the syringe barrel to expel the dose of medicament (M) and advances a needle shroud to a safe position (PS) to surround the injection needle after the medicament (M) has been at least partially delivered. The coupling shroud is decoupled from the plunger at a pre-determined second position (II) defined by an aperture formed into the housing.

10 Claims, 5 Drawing Sheets

(56) References Cited

U.S. PATENT DOCUMENTS

2007/0112310 A1  5/2007  Lavi et al.
2007/0129686 A1  6/2007  Daily et al.
2010/0280460 A1* 11/2010 Markussen ................. 604/195

FOREIGN PATENT DOCUMENTS

| WO | 2005097238  | 10/2005 |
| WO | 2009/062508 | 5/2009  |
| WO | 2010/146358 | 12/2010 |

* cited by examiner

AUTO-INJECTOR

CROSS REFERENCE TO RELATED APPLICATIONS

The present application is a U.S. National Phase Application pursuant to 35 U.S.C. §371 of International Application No. PCT/EP2011/073503 filed Dec. 21, 2011, which claims priority to European Patent Application No. 10196068.0 filed Dec. 21, 2010 and U.S. Provisional Patent Application No. 61/432,254, filed Jan. 13, 2011. The entire disclosure contents of these applications are herewith incorporated by reference into the present application.

TECHNICAL FIELD

The invention relates to an auto-injector for administering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved auto-injector.

The object is achieved by an auto-injector according to claim 1.

Preferred embodiments of the invention are given in the dependent claims.

In the context of this specification, the terms distal and proximal are defined from the point of view of a person receiving an injection. Consequently, a proximal direction refers to a direction pointing towards the body of a patient receiving the injection and a proximal end defines an end of an element that is directed towards the body of the patient. Respectively, the distal end of an element or the distal direction D is directed away from the body of the patient receiving the injection and opposite to the proximal end or proximal direction.

According to the invention, an auto-injector for administering a dose of a liquid medicament comprises
- a substantially cylindrical housing arranged to contain a pre-filled syringe,
- a syringe retainer slidably arranged with respect to the housing that mounts a pre-filled syringe with an injection needle, a plunger and a stopper for sealing a syringe barrel of the pre-filled syringe,
- a coupling shroud slidably arranged within the housing and releasably coupled to the plunger and
- a single drive means. Upon release, the single drive means is capable of driving the coupling shroud from a first position in the proximal direction. The proximal translatory movement of the coupling shroud with respect to the housing
  - translates the syringe retainer in the proximal direction to expose the injection needle of the pre-filled syringe,
  - depresses the plunger connected to the stopper into the syringe barrel to expel the dose of medicament and
  - advances a needle shroud to a safe position to surround the injection needle after the medicament has been at least partially delivered. The coupling shroud is decoupled from the plunger at a pre-determined second position defined by an aperture formed into the housing.

The mechanism of the auto-injector is arranged in a manner that a plurality of functions is executed by the single drive means. The injection needle is inserted into the skin of the patient, the plunger is translated to expel the medicament and the needle shroud is moved proximally to provide needle safety after the injection is completed by the action of the spring means. Conventional auto-injectors usually comprise a plurality of spring means to accomplish these tasks. The auto-injector according to the invention comprises only few parts and is particularly inexpensive to mass-produce. Consequently, the auto-injector is particularly suited as a single-use device that may be disposed after an injection has been carried out.

The coupling shroud is initially coupled to the plunger to translate the syringe retainer proximally, whereby the injection needle is inserted into the skin of the patient, and to depress the stopper into the syringe barrel to expel the medicament. A crucial step for designing the auto-injector with the single drive means is the decoupling of the plunger and the coupling shroud at the proper pre-determined second position, so that the same drive means may be used to advance the needle shroud after the medication has been completely or partially delivered. The pre-determined second position is defined by a longitudinal aperture in the housing.

In one possible embodiment of the invention, the pre-determined second position defined by the aperture is arranged in a manner that allows for a decoupling of the plunger from the coupling shroud before the stopper reaches a proximal end of the syringe barrel. This ensures that a reliable activation of the safety functions of the auto-injector are activated after the medicament has been at least partially delivered.

According to another possible embodiment of the invention, a coupling catch is arranged to abut against a shoulder formed to the plunger as a particularly simple and reliable means to releasably couple the plunger to the coupling shroud. The coupling shroud is moved by the action of the relaxing drive means in the proximal direction and coupled to the plunger connected to the stopper to insert the injection needle before the injection and to expel the medication during the injection.

The aperture formed into the lateral side of the housing at the second position allows the coupling catch to deflect radially outwards at the second position, so that the coupling shroud is decoupled from the plunger after the medicament is partially or completely delivered.

Preferably, the single drive means is arranged as a single compression spring. Compression springs are readily available and inexpensive drive means that may be used to cut down on production costs.

According to one possible embodiment of the invention, a rotating collar is rotatably arranged within the housing. The rotating collar creates friction to slow down a proximal movement of the needle shroud that is designed to rest onto the skin of the patient during the injection. The rotating collar acts as a dampening element that alleviates the pressure exerted upon the skin of the patient by the single drive means via the needle shroud and thus reduces the risk of injuries like bruises. Furthermore, the modulus of resilience of the single drive means may be chosen to be sufficiently large without having to worry about potential injury risks. Thus, the modulus of resilience of the single drive means is adapted to reliably provide an energy supply for a plurality of actions comprising, in particular, the advancing of the syringe retainer and the needle shroud, the displacement of the stopper to expel the medication and the decoupling of the plunger and the coupling shroud.

Preferably, the rotating collar comprises a pin that engages a helical recess formed into the needle shroud. The engagement of the helical recess and the pin forces the rotating collar to rotate around the needle shroud when the needle shroud is translated. This in particular dampens a proximal movement of the needle shroud and thus reduces the pressure exerted upon the skin of the patient by generating friction.

According to another possible embodiment of invention, the auto-injector comprises safety means that are arranged to cooperate with the needle shroud to prevent a release of the drive means when the needle shroud is in an advanced position and hence is not pushed against the skin of the patient at the injection site. This mechanism avoids an early release of the drive means and thus a prematurely expelling of the medicament. Furthermore, injuries resulting from an activation of the drive means when the auto-injector is not or not properly placed onto the skin of the patient are reduced.

In one possible embodiment of the invention, the safety means comprises an elastic bushing that engages the plunger and/or the coupling shroud. The elastic bushing is firmly attached to a proximal end of the housing and may engage the coupling shroud and/or the plunger to prevent an inadvertent release of the drive means.

In another possible embodiment of the invention, a release element is hinged to the lateral side of the housing. The safety means comprises a blocking element slidably arranged relative to the housing. Manual actuation of the release element causes the release element to pivot about a hinge to release the drive means. The blocking element is arranged to limit a pivoting movement of the release element when the needle shroud is in an advanced position and hence to prevent an activation of the drive means. The release element is allowed pivot about the hinge when the needle shroud is moved to a refracted position by pressing the needle shroud against the skin surface of the patient receiving the injection.

Preferably, the blocking element is arranged to block a distal movement of the needle shroud when the release element is manually actuated while the needle shroud is located in the advanced position. The pivoting release element may comprise an inward projection that is pushed radial inwards by manually actuating the release element to block a displacement of the needle shroud from the advanced position. The user is thus forced to perform the sequence of actions necessary to start the injection in the proper order. In particular, the user is forced to first push the needle shroud against the skin of the patient to translate the needle shroud to the retracted position. Subsequently, the release element is manually actuated to release the drive means.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
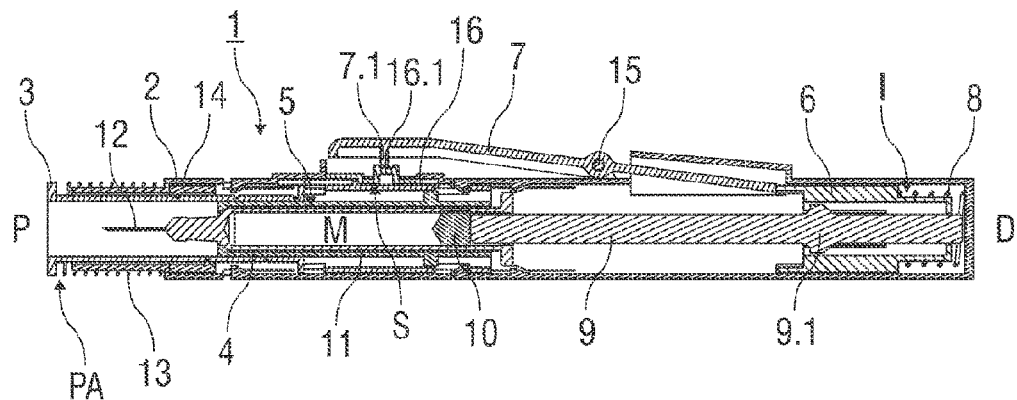
FIGS. 1A and 1B show two different sectional views of an auto-injector according to a first embodiment of the invention with a hinged release element before an injection.
Figure 1B:
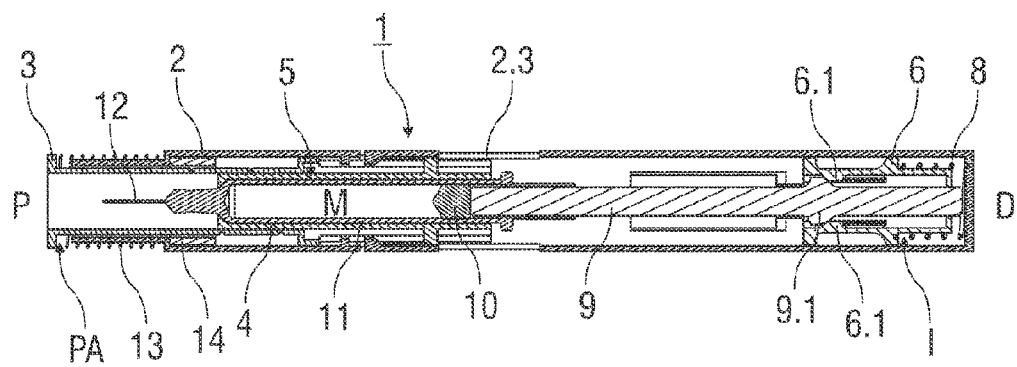

FIGS. 1A and 1B show two sectional views of an essentially cylindrical auto-injector 1 according to a first embodiment of the invention, wherein the sectional plane shown in FIG. 1A is oriented perpendicularly to the one shown in FIG. 1B. The auto-injector 1 comprises a housing 2, a proximal needle shroud 3, a syringe retainer 4 adapted to mount and move translatably with a pre-filled syringe 5 within the housing 2, a coupling shroud 6 slidably arranged within the housing 2 and a release element 7 hinged to a lateral side of the substantially cylindrical housing 2 of the auto-injector 1.

A single drive means 8 is arranged between the distal end of the housing 2 and the coupling shroud 6 to bias the coupling shroud 6 in a proximal direction P towards the skin of a patient receiving an injection.

According to one possible embodiment of the invention, the drive means 8 is arranged as a single, conventional compression spring.

The coupling shroud 6 is releasably coupled to a plunger 9 that is connected to a stopper 10 fluid-tightly sealing a distal end of a syringe barrel 11 containing a dose of a medicament M. An inner cavity of the syringe barrel 11 is in fluid communication with an injection needle 12, so that the dose of the medicament M may be expelled through the injection needle 12 by displacing the stopper 10 in the proximal direction P.

Before the injection, the coupling shroud 6 abuts against a distal end of the release element 7 to releasably retain the coupling shroud 6 in a first position I, wherein the coupling shroud 7 is located at a distal end of the housing 2. The drive means 8 is compressed, so that the coupling shroud 6 is strongly biased in the proximal direction P.

The plunger 9 extends from the syringe barrel 11 in a distal direction D and comprises a shoulder 9.1 of increased diameter. The coupling shroud 6 comprises an inwardly protruding coupling catch 6.1 that bears against the shoulder 9.1 so that the plunger 9 and the coupling shroud 6 may be jointly moved in the proximal direction P by the action of the relaxing drive means 8.

The proximal end of the needle shroud 3 is designed to be pushed against the skin surface of the patient during the injection. Edges of the needle shroud 3 may thus be smoothed to avoid injuries. The needle shroud 3 is slidably arranged within the housing 2 of the auto-injector 1, so that the needle shroud 3 may be pushed from an advanced position PA shown in FIGS. 1A and 1B in the distal direction D. A biasing means 13 bears against the needle shroud 3 and the housing 2 to bias the needle shroud 3 towards the advanced position PA.

An annular rotating collar 14 engages an outer surface of the needle shroud 3. The rotating collar 14 rotates around an axis of the substantially cylindrical auto-injector 1 when the needle shroud 3 is longitudinally displaced in the proximal and/or the distal direction P, D. The rotating collar 14 acts as a damping means that creates friction to slow down the movement of the needle shroud 3 and to reduce the pressure exerted onto the skin of the patient receiving the injection.

The release element 7 hinged to the housing 2 works like a see-saw: a proximal section may be pushed radially inwards, whereby the release element 7 pivots about a hinge 15, so that the distal section of the release element 7 moves radially outwards and the coupling shroud 6 is disengaged to release the drive means 8.

The auto-injector 1 comprises safety means S that prevents an early release of the drive means 8. The safety means S ensures that the needle shroud 3 is pushed against the skin of the person receiving the injection before the drive means 8 may be released.

According to the first embodiment of the invention, the safety means S comprises a blocking element 16 slidably arranged with the housing 2. When the needle shroud 3 is positioned in the advanced position PA, the blocking element 16 is positioned to prevent a pivoting movement of the release element 7 and thus a release of the coupling shroud 6. A radially outwards protruding blocking projection 16.1 of the blocking element 16 is located opposite to an inward protrusion 7.1 formed to the release element 7. If the proximal section of the release element 7 is pushed inwards, the inward protrusion 7.1 abuts against the blocking projection 16.1 to limit the pivoting movement of the release element 7, so that a release of the coupling shroud 6 and the drive means 8 is prevented.

Figure 2:
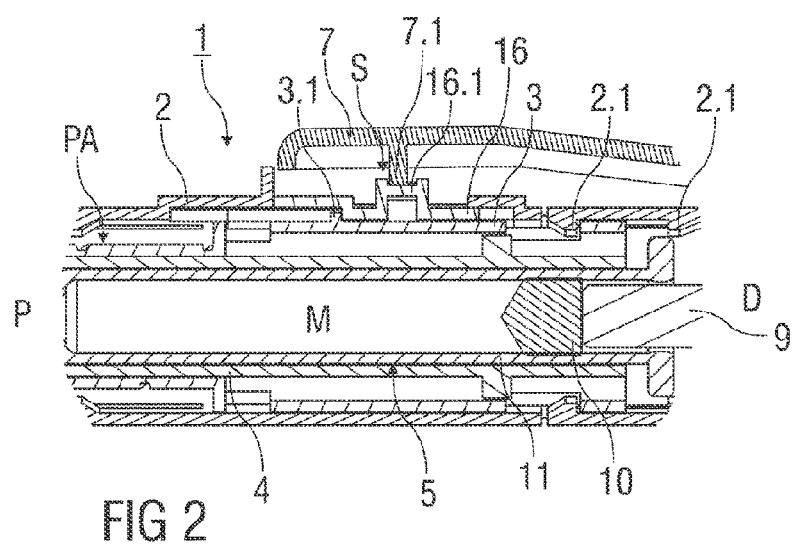
FIG. 2 is an expanded sectional view of the auto-injector according to the first embodiment, wherein the release element is blocked to prevent an inadvertent release of a drive means.

FIG. 2 shows a proximal section of the auto-injector 1 in a sectional view with the blocking element 16 positioned to prevent an inadvertent actuation of the hinged release element 7 to release the drive means 8.

A distal end of the needle shroud 3 is clipped to the housing 2 and retained between two inwardly protruding retaining protrusions 2.1 formed into an inner surface of the housing 2. The two retaining protrusions 2.1 are longitudinally displaced from each other to limit the range of axial displacement of the needle shroud 3 with respect to the housing 2. A boss 3.1 formed into an outer surface of the needle shroud 3 bears against an inner surface of the blocking element 16, so that the blocking element 16 may move with the needle shroud 3 in the proximal direction P to deblock the release element 7.

Figure 3:
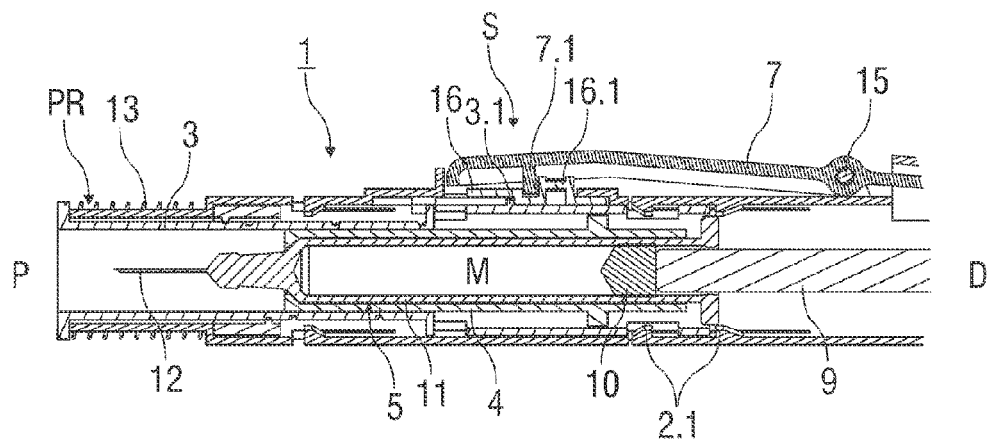
FIG. 3 is an expanded sectional view of the hinged release element that is actuated to release the drive means.

The blocking projection 16.1 comprises a central indention that forces a user of the auto-injector 1 to perform a sequence of actions necessary to inject the dose of the medicament M in the proper order. If the release element 7 is pushed inwards before the needle shroud 3 is moved proximally from the advanced position PA towards a retracted position PR (see FIG. 3) by pushing the needle shroud 3 towards the skin of the patient, the inward projection 7.1 is retained in the central indentation of the blocking projection 16.1, so that both the longitudinal displacement of the needle shroud 3 and the pivoting movement of the release element 7 is blocked.

A proper sequence of actions for injecting the dose of the medicament M is described in the following. First, the user pushes the needle shroud 3 against the skin to move the needle shroud 3 distally to the retracted position PR illustrated in FIG. 3. The blocking element 16 jointly moves with the needle shroud 3 in the distal direction D, so that the release element 7 may be manually actuated to pivot about the hinge 15, whereby the drive means 8 are released.

Upon release of the drive means 8, the coupling shroud 6 is urged in the proximal direction P. The single and fully compressed drive means 8 drives the coupling shroud 6 and the plunger 9 coupled thereto in the proximal direction P. The coupling shroud 6 first pushes the syringe retainer 4 by means of plunger 9, stopper 10 and the friction between stopper 10 and syringe 11 proximally to insert the injection needle 12 into the skin of the patient and a first clip connection 2.2 formed into a lateral side of the housing 2 latches to an outward protrusion 4.1 of the syringe retainer 4, as illustrated in more detail in FIG. 4B.

The syringe retainer 4 and the pre-filled syringe 5 mounted thereto is now locked to the housing 2. The coupling shroud 6 is moved further in the proximal direction P by the action of the relaxing drive means 8, whereby the plunger 9 is depressed into the syringe barrel 11 to expel the dose of the medicament M contained therein through the injection needle 12.

Figure 4A:
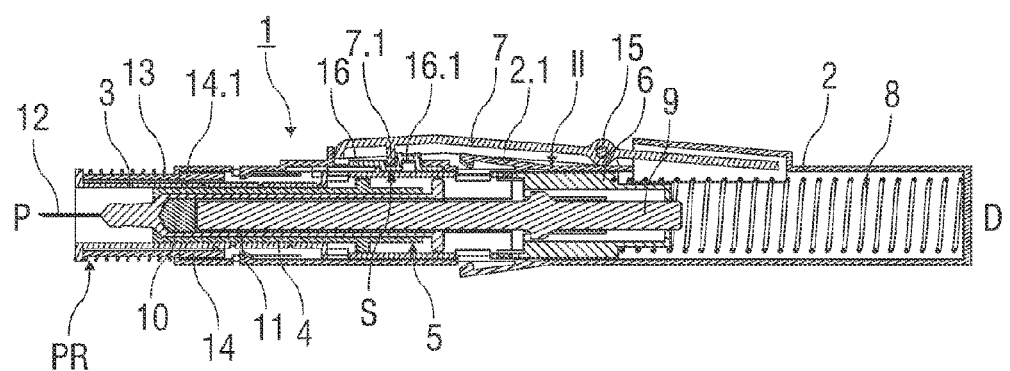
FIGS. 4A and 4B are two different sectional views of the auto-injector according to the first embodiment after a drug has been delivered.
Figure 4B:
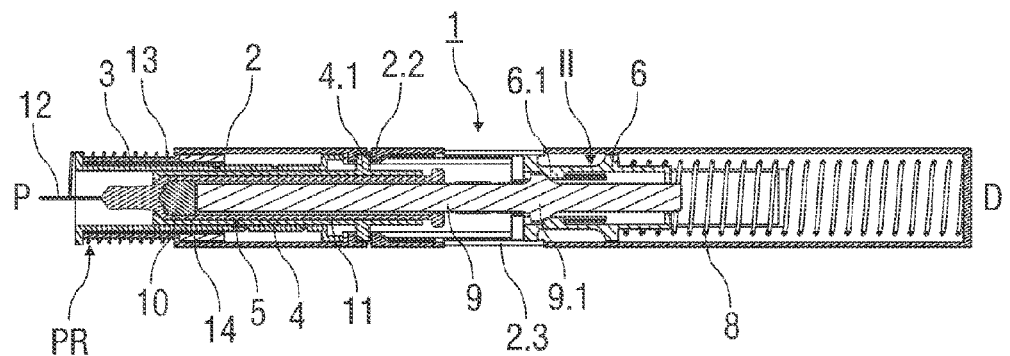

FIGS. 4A and 4B show two sectional views of the auto-injector 1 according to the first embodiment of the invention with the plunger 9 fully depressed within the syringe barrel 11. The dose of the medicament M has been delivered beneath the skin of the patient. The coupling shroud 6 is located in an intermediate second position II. The drive means 8 is not yet completely discharged and biases the coupling shroud 6 in the proximal direction P. The shoulder 9.1 engages a ramp of the coupling catch 6.1 to deflect the coupling catch 6.1 in a radial outward direction. An aperture 2.3 is formed into the housing 2 to allow for a radial outward deflection of the coupling catch 6.1, so that the coupling catch 6.1 overcomes the shoulder 9.1 decoupling the coupling shroud 6 from the plunger 9.

In a possible embodiment of the invention, the aperture 2.3 defining the second position II is located at a longitudinal position along the housing 2 that allows for a full depression of the plunger 9 completely emptying the syringe barrel 11 before the plunger 9 is decoupled from the coupling shroud 6.

Alternatively, the aperture 2.3 defining the second position II may be located at a longitudinal position along the housing 2 that allows for an adjustment space accounting for manufacturing tolerances. The adjustment space is dimensioned as to allow for a reliable decoupling of the plunger 9 from the coupling shroud 6 even if the parts constituting the auto-injector 1 comprise mismatch in mould or are slightly misaligned. In this alternative embodiment, the dose of the medicament M may or may not be completely expelled before the plunger 9 is decoupled from the coupling shroud 6.

The retaining protrusions 2.1 are elastically supported and may be deflected radially outwards to release the needle shroud 3. The coupling shroud 6 engages a ramp of the retaining protrusions 2.1 and splays the retaining protrusions 2.1 outwards, whereby the needle shroud 3 is released and allowed to move proximally from the retracted position PR towards an extended safe position PS.

The drive means 8 is still partially loaded when the coupling shroud 6 is located in the second position II. In a possible embodiment of the invention the biasing force of the drive means 8 exerted on the coupling shroud 6 in the second position II is about 10 N.

The coupling shroud 6 bears against a distal end of the needle shroud 3, so that the needle shroud 3 may be moved to the safe position PS by the action of the further relaxing drive means 8. As the biasing force exerted onto the needle shroud 3 by the drive means 8 may be relatively large and could even bruise the patient, the rotating collar 14 is arranged within the housing 2 to partially absorb the excess energy of the drive means 8 and slow down the proximal movement of the needle shroud 3 by generating friction.

Figure 5:
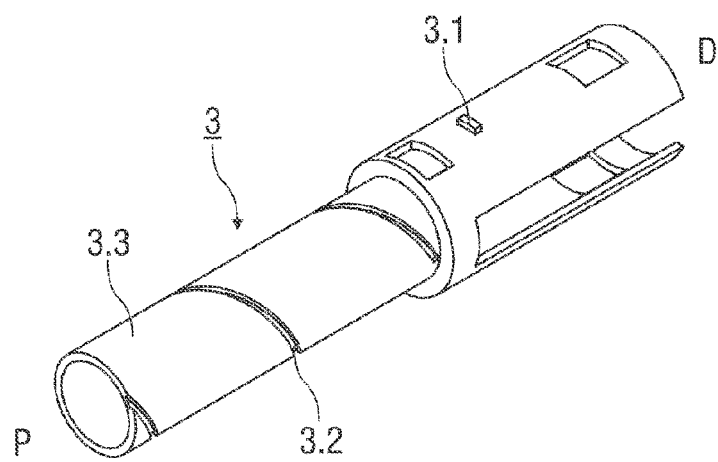
FIG. 5 is an isometric view of a needle shroud.
Figure 6A:
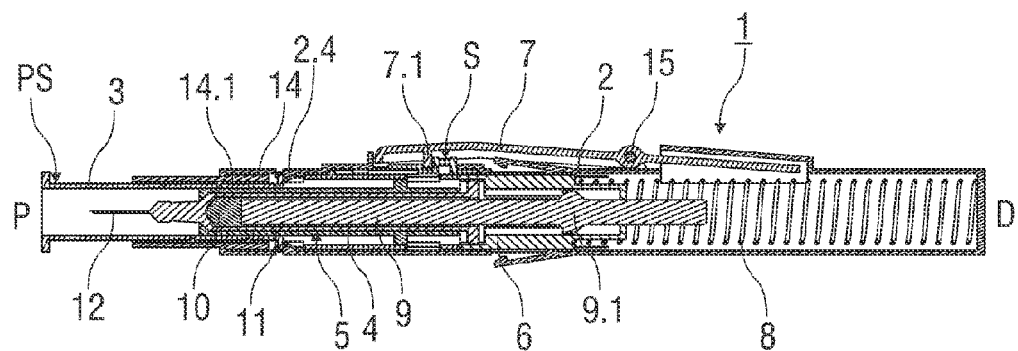
FIGS. 6A and 6B are two different sectional views of the auto-injector according to the first embodiment after an injection has been performed.

FIG. 5 shows an isometric view of the needle shroud 3. A helical recess 3.2 is formed into a tubular proximal section 3.3 of the needle shroud 3. The proximal section 3.3 of the needle shroud 3 is inserted into the annular rotating collar 14, wherein a pin 14.1 formed to an inner surface of the rotating collar 14 protrudes into the helical recess 3.2 as shown in FIG. 6A. The linear translatory movement of needle shroud 3 towards the safe position PS thus causes the rotating collar 14 to rotate within the housing 2 around the axis of the auto-injector 1.

Figure 6B:
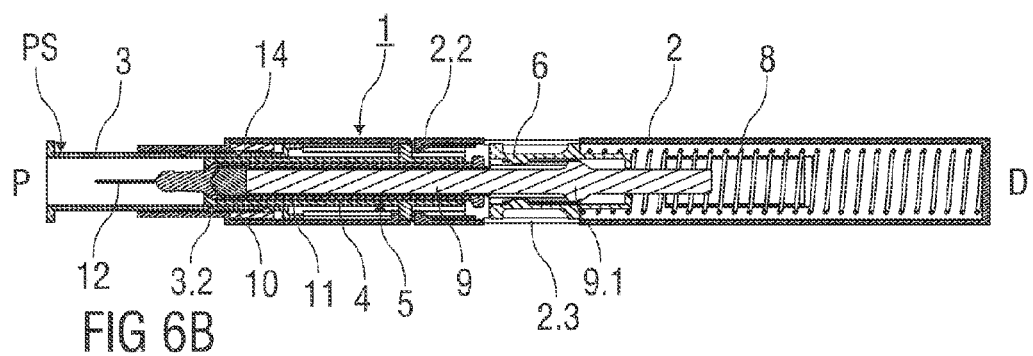

FIGS. 6A and 6B show two different sectional views of the auto-injector 1 according to the first embodiment of the invention after the injection has been performed. The needle shroud 3 is permanently locked to the safe position PS by a second clip connection 2.4 formed into the housing 2. The needle shroud 3 surrounds the injection needle 12 and extends a suitable distance proximally beyond the needle tip to avoid accidental needle stick injuries after the auto-injector 1 has been used.

Figure 7A:
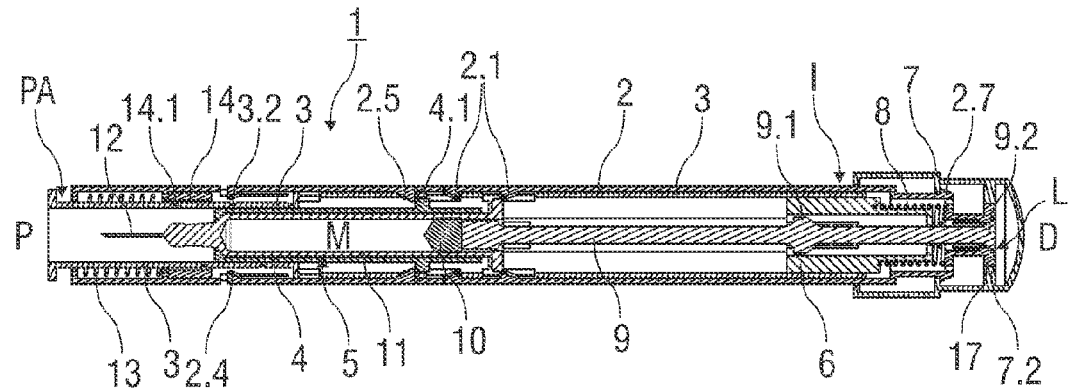
FIGS. 7A and 7B are two different sectional views of an auto-injector according to a second embodiment of the invention.
Figure 7B:
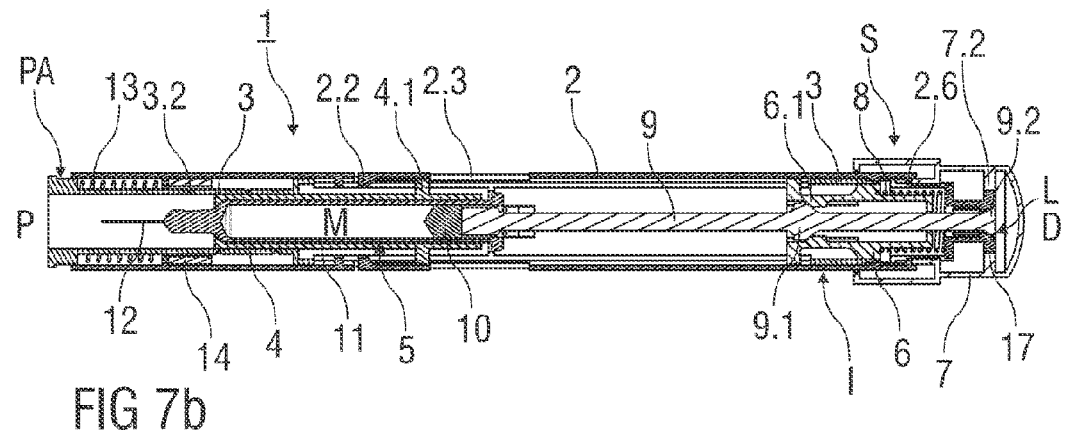

FIGS. 7A and 7B show two different sectional views of an auto-injector 1 according to a second embodiment of the invention before the injection. The sectional plane shown in FIG. 7A is oriented perpendicularly to the sectional plane shown in FIG. 7B.

The needle shroud 3 of the auto-injector 1 according to the second embodiment substantially extends over the axial length of the housing 2. Before the injection, the needle shroud 3 is mounted to the housing 2 by the retaining protrusions 2.1 that protrude into orifices formed into a lateral side of the needle shroud 3. The orifices comprise a longitudinal length that allows the needle shroud 3 to be slid from the advanced position PA to the retracted position PR.

A retaining catch 2.5 is formed to an inner surface of the housing 2 and protrudes through an opening formed into the needle shroud 3 to releasably mount the syringe retainer 4 retaining the pre-filled syringe 5. The retaining catch 2.5 comprises a bevelled ramp and is deflectable in a radial outward direction. The retaining catch 2.5 latches to the outward protrusion 4.1 formed to the outer surface of the syringe retainer 4 when the needle shroud 3 is in the advanced position PA The needle shroud 3 abuts against the bevelled ramp of the retaining catch 2.5 when the needle shroud 3 is moved from the advanced position PA in the distal direction D, whereby the retaining catch 2.5 is deflected in a radial outward direction and disengages the outward protrusion 4.1, so that the syringe retainer 4 may be moved in the proximal direction P.

Figure 8:
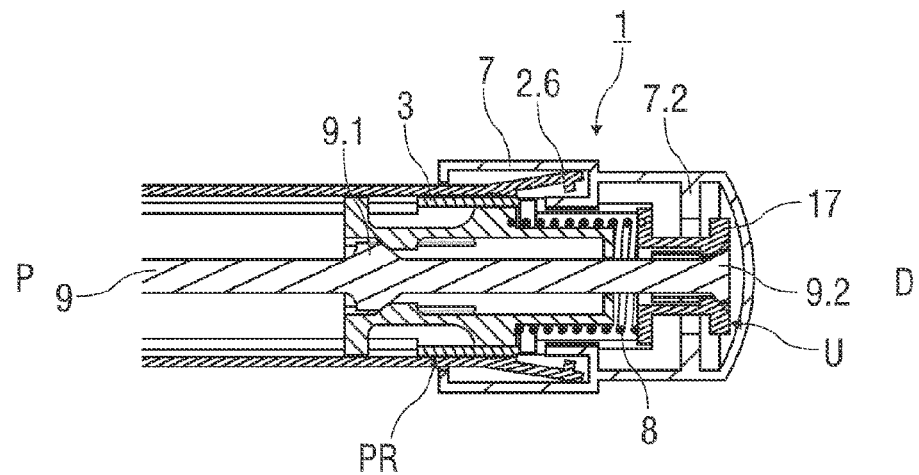
FIG. 8 is a sectional view of a distal end section of the auto-injector according to the second embodiment of the invention.

The release element 7, shown in more detail in FIG. 8, is arranged as a push button and mounted to a distal end of the housing 2. The release element 7 may be pushed in the proximal direction P to release the drive means 8 when the needle shroud 3 is in the retracted position PR, whereas the release element 7 and thus the release of the drive means 8 is blocked when the needle shroud 7 is in the advanced position PA.

According to the second embodiment of the invention, the safety means S that prevent the early release of the drive means 8 comprises clips 2.6 that may deflect in a radial outward direction and a bushing 17 locking the plunger 9 before use of the auto-injector 1.

Before the auto-injector 1 is used, the clips 2.6 formed to the housing 8 latch to the release element 7. (See FIG. 7*b*) The clips 2.6 block the movement of the release element 7 in the proximal direction P, so that a manual actuation of the release element 7 is prevented as long as the needle shroud 3 is in the advanced position PA. A distal movement of the release element 7 is blocked by a first detent 2.7 engaging an inner surface of the release element 7.

The clip 2.6 comprises a ramp that the needle shroud 3 engages when pushed distally from the advanced position PA to the refracted position PR, whereby the clip 2.6 is deflected radially outwards to disengage the needle shroud 3. The release element 7 may be pushed in the proximal direction P when the needle shroud 3 is in the retracted position PR.

The plunger 9 comprises a distal end 9.2 of increased diameter that is retained in the bushing 17 firmly attached to a distal end of the housing 2. The bushing 17 comprises an inner surface corresponding to the distal end 9.2 of the plunger 9 that engages the distal end 9.2 in a locked position L to lock the plunger 9 and the coupling shroud 6 coupled thereto to the housing 2 before use of the auto-injector 1. The bushing 17 abuts radially against an annular inner collar 7.2 of the release element 7 in the locked position L shown in FIGS. 7A and 7B. A radial outward deflection of the bushing 17 releasing the plunger 9 is thus prevented.

FIG. 8 shows a sectional view of a distal end section of the auto-injector 1 according to the second embodiment of the invention. The needle shroud 3 is located in the retracted position PR and the release element 7 is pushed in the proximal direction P, so that the bushing 17 disengages the annular inner collar 7.2 of the release element 7. The bushing 17 is positioned in an unlocked position U and may deflect outwardly to release the plunger 9.

Furthermore, the bushing 17 acts as a counter bearing for the drive means 8 bearing against the bushing 17 in the distal direction D.

Figure 9A:
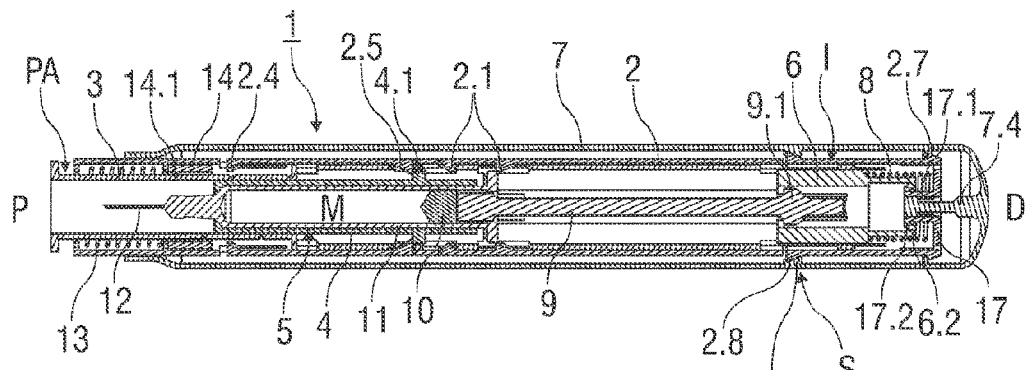
FIGS. 9A and 9B are two different sectional views of an auto-injector according to a third embodiment of the invention.
Figure 9B:
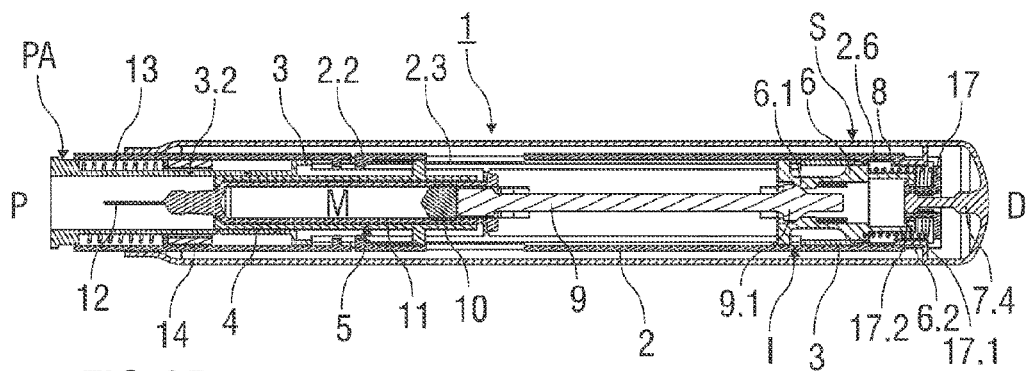

FIGS. 9A and 9B show two different sectional views of an auto-injector 1 according to a third embodiment of the invention, wherein the release element 7 is arranged as an outer sleeve extending over a substantial length of the auto-injector 1.

According to the third embodiment of the invention, the safety means S that prevent the early release of the drive means 8 comprise clips 2.6, second and third detents 2.8, 7.3, a locking catch 6.2 formed to the coupling shroud 6 and the bushing 17 that comprises an inner sleeve 17.1 receiving a lug 7.4, wherein the locking catch 6.2 latches to a collar 17.2 of the inner sleeve 17.1.

The release element 7 of the third embodiment is gripped by a user to perform the injection. When the needle shroud 3 is in the advanced position PA, the proximal displacement of the release element 7 is blocked by the clips 2.6 in a similar manner as in the second embodiment described herein above.

Additionally, the release element is releasably retained in position before the injection by the second and the third detents 2.8, 7.3 respectively formed to an outer surface of the housing 2 and to an inner surface of the release element 7, wherein the second and third detents 2.8, 7.3 comprise correspondingly shaped ramps facing each other.

The bushing 17 of the third embodiment comprises the inner sleeve 17.1 that receives the lug 7.4 formed to an inner surface of the release element 7. A proximal end of the lug 7.4 snugly fits in the central aperture of the inner sleeve 17.1, so that an inward deflection of the inner sleeve 17.1 is prevented.

The inner sleeve 17.1 comprises a collar 17.2. An inwardly protruding locking catch 6.2 of the coupling shroud 6 latches to the collar 17.2 before use of the auto-injector 1 to releasably retain the coupling shroud 6 in the first position I.

Figure 10:
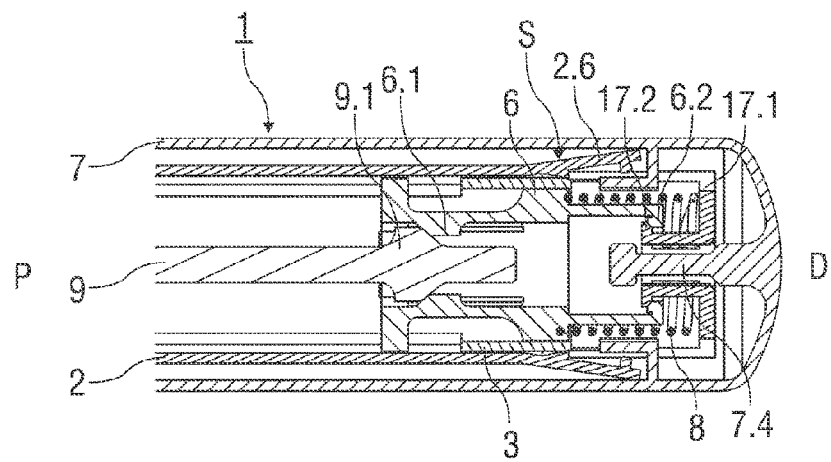
FIG. 10 is a sectional view of a distal end section of the auto-injector according to the third embodiment of the invention.

FIG. 10 shows a sectional view of a distal end section of the auto-injector 1 according to the third embodiment of the invention. The release element 7 is actuated and moved in the proximal direction P. The proximal end of the lug 7.4 disengages the inner sleeve 17.1 of the bushing 17, so that the inner sleeve 17.1 may bend radially inwards, whereby the locking catch 6.2 disengages the collar 17.2 and releases the coupling shroud 8 and the drive means 8.

The invention claimed is:

1. Auto-injector for administering a dose of a liquid medicament (M), comprising:
a substantially cylindrical housing arranged to contain a pre-filled syringe,
a syringe retainer slidably arranged with respect to the housing that mounts a pre-filled syringe with an injection needle, a plunger and a stopper for sealing a syringe barrel,
a coupling shroud slidably arranged within the housing and releasably coupled to the plunger and
a single drive means capable of, upon release:
driving the coupling shroud from a first position (I) in the proximal direction (P), wherein the proximal translatory movement of the coupling shroud with respect to the housing,
translates the syringe retainer in the proximal direction (P) to expose the injection needle of the pre-filled syringe,
depresses the plunger connected to the stopper into the syringe barrel to expel the dose of medicament (M) and
advances a needle shroud to a safe position (PS) to surround the injection needle after the medicament (M) has been at least partially delivered,
wherein the coupling shroud is decoupled from the plunger at a pre-determined second position (II) defined by an aperture formed into the housing,
wherein a coupling catch is arranged to abut against a shoulder formed to the plunger to releasably couple the plunger to the coupling shroud.

2. An auto-injector according to claim 1, wherein the pre-determined second position (II) defined by the aperture is arranged in a manner that allows for a decoupling of the plunger from the coupling shroud before the stopper reaches a proximal end of the syringe barrel.

3. An auto-injector according to claim 1, wherein the aperture allows the coupling catch to deflect radially outwards to decouple the coupling shroud from the plunger at the second position (II).

4. An auto-injector according to claim 3, wherein the rotating collar comprises a pin that engages a helical recess formed into the needle shroud.

5. An auto-injector according to claim 1, wherein the single drive means is arranged as a single compression spring.

6. An auto-injector according to claim 1, wherein a rotating collar is rotatably arranged within the housing for creating friction to slow down a proximal movement of the needle shroud.

7. An auto-injector according to claim 1, wherein safety means (S) are arranged to cooperate with the needle shroud to prevent a release of the drive means when the needle shroud is in an advanced position (PA).

8. An auto-injector according to claim 7, wherein the safety means (S) comprise a bushing that engages the plunger and/or the coupling shroud to prevent the release of the drive means.

9. An auto-injector according to claim 7, wherein the safety means (S) comprises a blocking element that is slidably arranged relative to the housing, wherein the blocking element is arranged to limit a pivoting movement of a release element hinged to lateral side of the housing when the needle shroud is in the advanced position (PA) and wherein the blocking element is arranged to allow the release element to pivot about a hinge when the needle shroud is in a retracted position (PR).

10. An auto-injector according to claim 9, wherein the blocking element is arranged to block a distal movement of the needle shroud when the release element is manually actuated while the needle shroud is located in the advanced position (PA).

* * * * *